United States Patent [19]
Oshlack et al.

[11] Patent Number: 6,077,533
[45] Date of Patent: *Jun. 20, 2000

[54] POWDER-LAYERED ORAL DOSAGE FORMS

[75] Inventors: Benjamin Oshlack, New York; Frank Pedi, Yorktown Heights, both of N.Y.

[73] Assignee: Purdue Pharma L.P., Norwalk, Conn.

[*] Notice: This patent is subject to a terminal disclaimer.

[21] Appl. No.: 09/005,864

[22] Filed: Jan. 12, 1998

Related U.S. Application Data

[63] Continuation-in-part of application No. 08/760,724, Dec. 5, 1996, abandoned, which is a continuation of application No. 08/431,359, Apr. 28, 1995, abandoned, which is a continuation-in-part of application No. 08/249,150, May 25, 1994, Pat. No. 5,411,745.

[51] Int. Cl.$^7$ ...................................................... A61K 9/62
[52] U.S. Cl. .......................... 424/461; 424/458; 424/490; 424/493; 427/2.14
[58] Field of Search ..................................... 424/451, 452, 424/456, 457, 458, 459, 460, 461, 462, 490, 492, 493, 494; 427/2.14

[56] References Cited

U.S. PATENT DOCUMENTS

| | | | |
|---|---|---|---|
| 2,738,303 | 3/1956 | Blythe | 167/82 |
| 3,639,170 | 2/1972 | Hutton et al. | 127/31 |

(List continued on next page.)

FOREIGN PATENT DOCUMENTS

| | | | |
|---|---|---|---|
| 5229961 | 7/1993 | Japan | A61K 47/12 |
| 8601717 | 3/1986 | WIPO | A61K 31/44 |
| WO 9307861 | 4/1993 | WIPO | A61K 9/50 |

OTHER PUBLICATIONS

Kaiko, et al. "A single–dose study of the effect of food ingestion and timing of dose administration on the pharmacokinetic profile of 30 mg sustained–release morphine sulfate tablets", *Current Therapeutic Research*, pp. 869–878, vol. 47, No. 5, May 1990.

Kaiko, et al. "Controlled–release morphine bioavailability (MS Contin® tablets) in the presence and absence of food" *The Hospice Journal,* pp. 17–30, vol. 6(4), 1990.

Gourlay, et al. "the reproducibility of bioavailability of oral morphine from solution under fed and fasted conditions", *Journal of Pain and Symptom Management,* pp. 431–436, vol. 6, No. 7, Oct. 1991.

Gourlay, et al., "Influence of a high–fat meal on the absorption of morphine from oral solutions", *Clin Pharmacol Ther,* pp. 403–468, Oct. 1989.

MSIR® Package Insert, The Purdue Frederick Company, Feb. 11, 1993 (F3154).

MSIR® Capsules Prescribing Information Booklet, The Purdue Frederick Company, Feb. 11, 1993(PR101/L149).

MSIR®, Product Information Pamphlet (PR 104/L131), The Purdue Frederick Company, Copyright 1993, which includes the following documents: PR108/L233; PR107/L232; and PR100B/L123.

The Merck Index, 11th Edition, Susan Budavari, Editor, Published by Merck & Co., Inc., Rahway, N.J., p. 5224, 1989.

Martindale, The Extra Pharmacopoeia, 25th Edition, p. 54, Edited by James E.F. Reynolds, published by the Pharmaceutical Press, London, 1982.

*Primary Examiner*—Robert H. Harrison
*Attorney, Agent, or Firm*—Davidson, Davidson & Kappel, LLC

[57] ABSTRACT

An oral dosage form of morphine is formulated by powder-layering an homogeneous mixture of morphine sulfate and hydrous lactose impalpable onto inert beads to obtain a multiparticulate product. A plurality of the powder-layered beads may be administered either in immediate release form or in an extended release form by coating with a hydrophobic material. In addition, multi-particulate oral dosage forms containing therapeutically effective agents containing a plurality of pharmaceutically acceptable inert beads powder-layered with homogeneous mixture of a therapeutically effective agent and hydrous lactose impalpable are also disclosed. A method of preparing the dosage forms as well as a method preparing spheroids containing the homogeneous mixture of therapeutically effective agent and hydrous lactose impalpable are also disclosed.

34 Claims, 3 Drawing Sheets

U.S. PATENT DOCUMENTS

| | | | |
|---|---|---|---|
| 3,845,770 | 11/1974 | Theeuwes et al. | 128/260 |
| 3,916,889 | 11/1975 | Russell | 128/145.8 |
| 4,063,064 | 12/1977 | Saunders et al. | 219/121 |
| 4,088,864 | 5/1978 | Theeuwes et al. | 219/121 LM |
| 4,213,977 | 7/1980 | Schane, Jr. et al. | 424/451 |
| 4,828,840 | 5/1989 | Sakamoto et al. | 424/474 |
| 5,026,560 | 6/1991 | Makino et al. | 424/494 |
| 5,132,142 | 7/1992 | Jones et al. | 427/196 |
| 5,133,974 | 7/1992 | Paradissis et al. | 424/480 |
| 5,167,964 | 12/1992 | Muhammad et al. | 424/482 |
| 5,202,128 | 4/1993 | Morella et al. | 424/469 |
| 5,260,072 | 11/1993 | Roche et al. | 424/464 |
| 5,382,434 | 1/1995 | de Haan et al. | 424/465 |
| 5,384,130 | 1/1995 | Kamada | 424/461 |
| 5,395,627 | 3/1995 | Dopper et al. | 424/489 |
| 5,401,502 | 3/1995 | Wunderlich et al. | 424/195.1 |
| 5,405,616 | 4/1995 | Wunderlich et al. | 424/451 |
| 5,411,745 | 5/1995 | Oshlack et al. | 424/456 |
| 5,478,577 | 12/1995 | Sackler et al. | 424/489 |
| 5,527,543 | 6/1996 | Dopper et al. | 424/489 |
| 5,574,150 | 11/1996 | Yaginuma et al. | 536/56 |
| 5,662,936 | 9/1997 | Haan et al. | 424/479 |
| 5,672,360 | 9/1997 | Sackler et al. | 424/490 |

POWDER-LAYERED ORAL DOSAGE FORMS

This application is a continuation-in-part of U.S. patent application Ser. No. 08/760,724, filed on Dec. 5, 1996, now abandoned; which in turn is a continuation of U.S. patent application Ser. No. 08/431,359, filed on Apr. 28, 1995, now abandoned; which in turn is a continuation-in-part of U.S. patent application Ser. No. 08/249,150, filed on May 25, 1994, now U.S. Pat. No. 5,411,745.

BACKGROUND OF THE INVENTION

One method of obtaining pharmaceutical products involves the use of an inert spherical bead which is coated with a drug in powder form. This technique, referred to in the art as "powder layering", generally involves the surface of the beads being coated with a binder solution, with the drug being applied onto the beads in powder form. This technique is usually suitable for the preparation of a wide range of drugs in immediate release form.

Powder layering techniques are well-known in the art, and are generally considered to work best with drugs which are freely soluble in water. Such drugs may be powder-layered directly onto the surface of tacky inert beads alone, or with additional excipients. In certain instances, it is preferable to use a spheronizing agent to add in the processing (layering) of the drug onto the beads. This is the case when the drug to be powder-layered is not freely water soluble.

U.S. Pat. No. 2,738,303 describes a sympathomimetic preparation which consists of small pellets coated with various thicknesses of a material slowly digestible or dispersible in the gastrointestinal tract. These pellets are prepared by placing small sugar pellets (non-pareil seeds) from 12–40 mesh in a rotating coating pan, wetting the sugar pellets using syrup U.S.P. or gelatin, and then coating them with a powder of the sympathomimetic. Thereafter, the powder-coated pellets are said to be extended by coating with a wax-fat coating such as a mixture of glyceryl monostearate and beeswax. In each of the examples, the non-pareil seeds were powder-layered to a low load (e.g., less than 50% of the total weight of the powder-layered pellet).

U.S. Pat. No. 5,026,560, which describes a method for producing powder-layered granules which are said to be spherical and which are said to be suitable for the application of a further coating for controlled release. Therein, granules are prepared by coating seed cores with a spraying powder contained a drug and a low substituted hydroxypropylcellulose powder, while at the same time spraying the seed cores with an aqueous binder. The powder contains 5–90 percent by weight of the low substituted hydroxypropylcellulose (preferably 10–60) and 2–70 percent by weight of drug (preferably 5–50 percent). The ratio of the aqueous binder to powder is said to be 1:1–1:2. The granules thereby produced are said to be spherical and to have an excellent hardness and disintegration.

WO 93/07861 describes multiphase microspheres containing a molecular compound dispersed in polymeric matrix which are said to achieve drug loading efficiencies between 80 and 100 percent. Particular ratios of water/oil emulsion to polymer and concentration of surfactant and dispersion media such as mineral oil is used to provide the beneficial result.

The use of organic solvents in the preparation of pharmaceutical formulations is considered undesirable because of inherent problems with regard to flammability, carcinogenicity, environmental concerns, cost, and safety in general. Therefore, it would be desirable to manufacture an immediate release morphine sulfate product or other therapeutically effective agent-containing product without the use of such organic solvents.

Many of the oral opioid analgesic formulations that are currently available in the market must be administered every four to six hours daily with a selected few formulated for less frequent 12 hour dosing. There is a need in the art to develop drug formulations which provide a duration of effect lasting longer than twelve hours such as a drug that may be administered to a patient only once a day.

Morphine, which is considered to be the prototypic opioid analgesic, has been formulated into 12 hour controlled-release formulations (i.e., MS Contin® tablets, commercially available from Purdue Frederick Company).

An orally administrable morphine formulation which would provide an extended duration of effect would be highly desirable. Such an oral sustained-release formulation of an opioid analgesic would provide effective steady-state blood levels (e.g., plasma levels) of the drug when orally administered such that a duration of effect greater than 12 hours, and more preferably, of about 24 hours or more, which formulation is fully bioavailable as well.

It would also be highly desirable to provide similar orally-administrable formulations containing therapeutically effective agents other than morphine.

OBJECTS AND SUMMARY OF THE INVENTION

It is object of the present invention to provide a method for providing a high-load immediate release multiparticulate formulation of morphine for oral administration.

It is another object of the present invention to an immediate release morphine sulfate multiparticulate oral dosage form which comprises powder-layered spheroids which are bioavailable which avoid the necessity for using organic solvents in the manufacture of the multiparticulate dosage form.

It is another object of the present invention to produce an immediate release dosage form of morphine which is bioequivalent and minimizes the food effect.

It is a further object of the present invention to provide an orally administered pharmaceutical dosage form of morphine that is suitable for once-a-day administration, which dosage form is bioavailable.

It is another object of the present invention to provide extended release formulations of drugs which are administered in relatively large amounts, in particular morphine, which formulations comprise powder-layered spheres which have been coated with a material suitable for providing the desired release rate of the drug.

It is a further object of the present invention to provide a method for providing extended release high-load powder-layered spheroid formulations of morphine.

It is an object of the present invention to provide a method for preparing high-load immediate release multiparticulate formulations containing therapeutically effective agents for oral administration.

It is another object of the present invention to provide an immediate release multiparticulate oral dosage form which comprises spheroids powder-layered with a therapeutically effective agent which is bioavailable and which avoids the necessity for using organic solvents in the manufacture thereof.

It is another object of the present invention to produce an immediate release dosage form of a therapeutically effective agent which is bioavailable and minimizes the food effect.

It is a further object of the present invention to provide an orally administered pharmaceutical dosage form of a therapeutically effective agent that is suitable for once-a-day administration, which dosage form is bioavailable.

It is another object of the present invention to provide extended release formulations of drugs which are administered in relatively large amounts in the form of powder-layered spheres which have been coated with a material suitable for providing the desired release rate of the drug.

The above objects and others are accomplished by the present invention, which relates in part to oral dosage forms comprising inert pharmaceutical beads which are powder-layered with a therapeutically effective agent. In certain preferred embodiments, the therapeutically effective agent is powder-layered onto the inert pharmaceutical beads until they attain a weight gain of greater than about 50%.

The present invention therefore is directed in part to the surprising discovery that in order to powder-layer certain therapeutically effective agents onto inert pharmaceutical beads, it is necessary to utilize a processing aid consisting essentially of hydrous lactose impalpable. The hydrous lactose impalpable is intimately admixed with the therapeutically effective agent prior to layering the therapeutically effective agent onto the inert pharmaceutical beads. The therapeutically effective agents included in the formulations of the present invention have a bulk density of from about 0.2 to about 0.8 g/ml and preferably from about 0.4 to about 0.75 g/ml. The hydrous lactose impalpable has a bulk density of from about 0.4 to about 0.9 g/ml and preferably from about 0.5 to about 0.7 g/ml.

The invention further relates to a method of preparing bioavailable oral dosage forms containing inert beads powder-layered with a therapeutically effective agent. The method includes determining the bulk density of the therapeutically effective agent, admixing the therapeutic agent with a pharmaceutically acceptable inert diluent comprising hydrous lactose impalpable powder having a bulk density of from about 75% to about 125% of the therapeutic agent's to form a homogeneous mixture; spraying an aqueous binder solution onto inert beads having a diameter from about 0.1 mm to about 3.0 mm, to provide the beads with a tacky surface; powder layering the homogeneous mixture of therapeutically effective agent and the diluent onto the beads once the beads have become tacky, to a weight gain of at least about 50%; drying the coated beads to obtain powder-layered beads having a smooth surface; and sieving the powder-layered beads to obtain a powder-layered multiparticulate product having a suitable range of particle size.

The invention further relates to a method of treating a mammal with an oral formulation containing a therapeutic agent. The method includes preparing a powder-layered multiparticulate formulation of therapeutically effective agent as set forth above, incorporating a plurality of the beads into unit doses each having a desired quantity of therapeutically effective agent, and orally administering the unit dose to a patient in need thereof. When orally administered, the unit dose of immediate release therapeutically effective agent provides effective blood plasma levels of therapeutically effective agent for about 4 hours, and the unit dose of extended release therapeutically effective agent provides effective blood plasma levels of therapeutically effective agent for about 12–24 hours.

The present invention is further related to a bioavailable extended release therapeutically effective agent dosage form for once-a-day oral administration. The dosage form comprises inert pharmaceutically acceptable beads having a diameter from about 0.1 mm to about 3 mm which have been powder-layered with therapeutically effective agent, and thereafter coated to a desired weight gain with a hydrophobic material to obtain the desired extended release of the drug when the formulation is exposed to fluids.

The above objects and others are accomplished by the present invention, which relates in part to oral dosage forms comprising inert pharmaceutical beads which are powder-layered with morphine sulfate. The resultant multiparticulate formulation is manufactured without the use of organic solvents.

In certain preferred embodiments, the morphine is powder-layered onto the inert pharmaceutical beads until they attain a weight gain of greater than about 50%.

The present invention therefore is directed in part to the surprising discovery that in order to powder-layer morphine sulfate onto inert pharmaceutical beads, it is necessary to utilize a processing aid consisting essentially of hydrous lactose impalpable. The hydrous lactose impalpable is intimately admixed with the morphine sulfate prior to layering the morphine sulfate onto the inert pharmaceutical beads.

The invention further relates to a method for preparing bioavailable, immediate release powder-layered beads of morphine sulfate suitable for oral administration comprising spraying an aqueous binder solution onto inert beads having a diameter from about 0.1 mm to about 3.0 mm, to provide said beads with a tacky surface; spraying a powder consisting of a homogeneous mixture of morphine sulfate and hydrous lactose impalpable powder onto the beads once the beads have become tacky, to a weight gain of at least about 50%; drying said coated beads to obtain powder-layered beads having a smooth surface suitable; and sieving the powder-layered beads to obtain a powder-layered multiparticulate product having a suitable range of particle size.

The invention further relates to a method of treating a patient for moderate to sever pain with a bioavailable immediate release opioid analgesic oral dosage form, comprising preparing a powder-layered multiparticulate formulation of morphine sulfate as set forth above, dividing the multiparticulate product into unit doses each having a desired quantity of morphine sulfate, and administering the unit dose to a patient suffering from moderate to sever pain. When orally administered, the unit dose of immediate release morphine sulfate provides effective blood plasma levels of morphine for about 4 hours, and the unit dose of extended release morphine sulfate provides effective blood plasma levels of morphine for about 12–24 hours.

The present invention is further related to a bioavailable extended release morphine dosage form for once-a-day oral administration. The dosage form comprises inert pharmaceutically acceptable beads having a diameter from about 0.1 mm to about 3 mm which have been powder-layered with morphine, and thereafter coated to a desired weight gain with a hydrophobic material to obtain the desired extended release of the drug when the formulation is exposed to fluids.

The hydrophobic material is selected from the group consisting of (i) an acrylic polymer such as copolymers of acrylic and methacrylic acid; (ii) an alkylcellulose such as ethylcellulose; (iii) other commonly used retardant coatings such as shellac, zein, and hydrophobic wax or waxy-type products either alone or in admixture with fatty (aliphatic) alcohols (e.g., cetostearyl alcohol), hydrogenated castor oil, or hydrogenated vegetable oil, or (iv) mixtures of any of groups (i)–(iii). The extended release oral dosage form provides the desired analgesic effect when administered, e.g., to a human patient, for at least about 24 hours.

For purposes of the present invention, the terms "beads" is meant to encompass any inert substrate having a size from about 0.1 mm to about 3.0 mm, and is deemed to encompass inert spheres, seeds, pellets, spheroids, cores, granules, particles, a compressed tablet made from these "beads", and the like.

The term "unit dose" is defined for purposes of the present invention as the total amount of beads needed to administer a desired dose of drug (e.g., morphine sulfate or a therapeutically effective agent) to a patient.

For purposes of the present invention, the term "therapeutically effective agent" is meant to encompass any pharmaceutically acceptance compound or composition and/or medicinal substance which can be administered to achieve a treatment effect in mammals. For example and without limitation, therapeutically effective agents include analgesics such as acetaminophen, gastrointestinal agents such as metaclopramide, narcotic analgesics such as codeine phosphate USP Special powder, codeine phosphate USP powder, codeine sulfate USP Medium crystals-fine and tramadol, broncodilating agents such as theophylline anhydrous and aminophylline USP, non-steroidal anti-inflammatory agents such as diclofenac sodium, antibiotic substances such as doxycycline metaphosphate sodium complex and vitamin products such as sodium ascorbate.

For purposes of the present invention, the term "environment of use" is meant to encompass an in-vitro testing apparatus, or an in-vivo location, such as the gastrointestinal tract.

The term "high-load" is defined for purposes of the present invention as encompassing any powder-layered beads which have a drug content of about 50% or more, by weight.

The term "low-load" is defined for the purposes of the present invention as encompassing any powder-layered beads which have a drug content of less than about 50%, by weight.

The term "bioavailable" is defined for the purposes of the present invention as the total amount of a drug substance that is absorbed to be available to provide the desired therapeutic effect after administration of a unit dosage form, as compared to the known reference drug product, as commonly determined and accepted by Governmental Regulatory Agencies, such as the United States FDA.

The term "bioavailablity" is defined for purposes of the present invention as the extent to which the drug (e.g., opioid analgesic) is absorbed from the unit dosage forms and becomes available at the site of drug action.

The term "immediate release" is defined for purposes of the present invention as the release of the drug (e.g., opioid analgesic) at such a rate that blood (e.g., plasma) levels are maintained within the therapeutic range but below toxic levels over a period of time of about 4 hours.

The term "extended release" is defined for purposes of the present invention as the release of the drug (e.g., opioid analgesic) at such a rate that blood (e.g., plasma) levels are maintained within the therapeutic range but below toxic levels over a period of time of about 12–24 hours or longer.

BRIEF DESCRIPTION OF THE DRAWINGS

The following drawing is illustrative of embodiments of the invention and is not meant to limit the scope of the invention as encompassed by the claims.

DETAILED DESCRIPTION

The inert beads which may be powder-layered in accordance with the present invention include commercially available nonpareils and seed cores. Suitable cores include Sugar Spheres, NF. Inert beads having a size from about $30/35$ to about $14/16$ may be used. Generally, the size of the beads is from about 0.1 mm to about 2.5 mm.

The binder which is used in the present invention may be any pharmaceutically acceptable binder known to those skilled in the art. Such binders include, for example, polyvinylpyrrolidone, natural and synthetic gums including gum arabic, hydroxypropylmethylcellulose, hydroxypropylcellulose, carboxymethylcellulose, methylcellulose, pullulan, dextrin, starch, and the like. The binder may be dissolved or dispersed in an aqueous or organic solution, or a mixture thereof. Aqueous binder solutions or dispersions are especially preferred. Suitable binding agents which are generally considered to be water-soluble include polyvinylpyrrolidone, hydroxypropylmethylcellulose, and maize starch. Many other water-soluble binding agents which would be suitable for use in conjunction with the present invention are known to those skilled in the art. In one preferred embodiment, and aqueous 5% polyvinylpyrrolidone solution is utilized as the binder solution.

The spraying powder comprising the drug may also include additional inert excipients, including glidants, diluents, stabilizers, coloring agents, and binders. Suitable glidants include, e.g., colloidal silicon dioxide and/or talc. Suitable diluents include, e.g., polysaccharides, monosaccharides, corn starch, and the like.

The morphine which is included in the formulations of the present invention is preferably included as the sulfate salt. Chemically, morphine sulfate is an opioid analgesic having the structure 7,8 didehydro-,5 α-epoxy-17-methylmorphinan-3,6 α-diol sulfate (2:1) salt pentahydrate.

In the immediate release formulations of the present invention, it is preferred that the unit dose contains from about 5 mg to about 60 mg of morphine (provided either as morphine base or a pharmaceutically acceptable morphine salt, such as morphine sulfate). In most preferred embodiments, the unit dose contains either 15 mg, 20 mg, or 30 mg, morphine (based on the sulfate salt thereof).

In the sustained release embodiment of the present invention, the unit dose contains from about 5 mg to about 800 mg morphine (provided as the sulfate salt), by weight.

Due to size constrictions for an oral dosage form, it is desirable in certain formulations of the present invention to provide the spheres with a high load of drug. In the high-load formulations of the present invention, the spheres comprise 50% or more drug, by weight. In certain preferred embodiments, the spheres comprise 70% or more drug, by weight.

It has been found by the inventors that morphine sulfate is not readily powder-layered onto the surface of inert pharmaceutical beads, the surfaces of which have been made tacky via the use of a binder. It is postulated that this is due in part to the fact that while morphine sulfate is soluble in water (16–24 grams in one liter of water), morphine sulfate is not freely soluble in water.

It has also been found by the inventors that certain therapeutically effective agents are not readily powder-layered onto the surface of inert pharmaceutical beads, the surfaces of which have been made tacky via the use of a binder. It is postulated that this is due in part to the fact that while these therapeutically effective agents may be somewhat soluble in water, they are not freely soluble in water. Even if the selected therapeutically effective agent is sufficiently water soluble, it would be desirable to have an alternative means for powder-layering available to the artisan.

Especially in the case of low-load morphine beads for immediate release formulations, due to the low dose of morphine a diluent is needed in order to properly (uniformly) distribute the morphine on the beads. This would also be the case for other low-load therapeutically effective agent beads prepared for immediate release formulations.

It is recognized among those skilled in the art that in cases where the drug to be powder-layered is not freely water soluble, such drugs may not be good candidates for powder-layering techniques, and it is often necessary to include an excipient which has an amorphous physical structure and which is highly water soluble in order to obtain an acceptable product. Morphine sulfate has been found to be such a drug. Other therapeutically effective agents, some of which are also not freely soluble have also been found to be candidates for powder layering.

To date, the practice has been to use a spheronizing agent, microcrystalline cellulose, mixed with the drug in extrusion/spheronization techniques. However, microcrystalline cellulose cannot be utilized in powder-layering techniques because it swells. Other typically used processing aids such as spray-dried lactose also have been found not to provide an acceptable product.

It has now been surprisingly discovered that by choosing a processing aid having a bulk density similar to that of morphine sulfate or that of other therapeutically effective agents, an pharmaceutically acceptable, bioavailable product can be obtained using powder-layering techniques. More particularly, it has been discovered that excellent results are obtained utilizing hydrous lactose impalpable as a processing aid. Hydrous lactose impalpable is commercially available, for example, from B. V. Hollandsche Melksuikerfabriek (HMS), Uitgeest, Holland. Typically, the hydrous lactose impalpable which is suitable for use in the present invention has a poured and tapped bulk density from about 0.4 to about 0.9 g/ml, and more preferably from about 0.5 g/ml to about 0.7 g/ml. Hydrous lactose impalpable is highly water soluble and has been discovered to readily layer onto the surface of tacky beads. The present invention also contemplates the inclusion of other inert pharmaceutically acceptable diluents in addition to or as alternatives to hydrous lactose impalpable. In this regard, the inert pharmaceutically acceptable diluents will have a bulk density of from about 75 to about 125% of that of the therapeutically effective agent. It is to be understood, however, that hydrous lactose impalpable is the preferred diluent.

In preferred embodiments, the morphine sulfate has a bulk density (poured and tapped) from about 0.2 g/ml to about 0.7 g/ml, more preferably from about 0.4 g/ml to about 0.5 g/ml, and is homogeneously mixed with hydrous lactose impalpable prior to powder layering the mixture onto the beads. In further embodiments, the therapeutically effective agents have a bulk density (poured and tapped) from about 0.2 g/ml to about 0.8 g/ml, more preferably from about 0.4 g/ml to about 0.75 g/ml, and is homogeneously mixed with hydrous lactose impalpable prior to powder layering the mixture onto the beads. A non-limiting list of therapeutically effective agents meeting this criteria is set forth below:

|  | Tapped Bulk Densities (g/ml) |
| --- | --- |
| Acetaminophen | 035–0.46 |
| Metoclopramide HCL | 0.5 |
| Codeine Phosphate USP Special Powder | 0.55 |
| Codeine Phosphate USP Powder | 0.25 |
| Codeine Sulfate USP Medium Crystals Fine | 0.7–0.5 |
| Doxycycline Metaphosphate Sodium Complex | 0.49 |
| Tramadol HCL* | 0.42 |
| Theophylline Anhydrous* | 0.44 |
| Aminophylline USP* | 0.62 |
| Diclofenac Sodium* | 0.31 |
| Sodium Ascorbate USP* | 0.66 |

*Bulk Densities performed at PRC

In preferred embodiments, the homogeneous powder mixture consists essentially of morphine sulfate or other therapeutically effective agent and hydrous lactose impalpable in a ratio from about 98:2 to about 2:98. Most preferably, the ratio of morphine sulfate or other therapeutically effective agent to hydrous lactose impalpable is from about 60:40 to about 40:60.

Although hydrous lactose impalpable is a known excipient to those skilled in the art, its previous known use was limited to use as a bulking agent or diluent in pharmaceutical dosage forms.

The homogeneous powder mixture can further include minor amounts of other pharmaceutically acceptable processing aids such as soluble diluents such as maltodextrin, sucrose, starches, certain grades of hydrophilic cellulose polymers, insoluble diluents such as talc, diacalcium phosphate and certain of hydrophobic cellulose polymers.

The powder-layered spheres of the invention may be prepared as follows. The drug together with any pharmaceutically necessary excipients (e.g., a glidant such as colloidal silicon dioxide) are mixed together. Prior to powder layering, a suitable binder solution (e.g., a 5% PVP aqueous solution) or cellulose solution or acrylic polymers, gums, etc., is prepared. The inert substrate (e.g., sugar spheres) are placed in, e.g., a Glatt rotor processor, and the binder solution is sprayed when operating conditions are attained. Once the sugar spheres (beads) are tacky, the powder comprising the drug is fed into the rotor processor. As the powder begins to layer on beads, both binder solution spray rate and powder feed rate are increased. Spray rate and powder feed rate proportions may be determined, e.g., by examining the tackiness beads during processing. The binder solution is continued to be sprayed onto the beads after all powder has been layered, to protect beads during drying. The powder-layered beads are then dried to a suitable loss on drying (LOD), for example to a moisture content of approximately 6%. The layered beads are then passed through a series of screens to remove undesirable sized beads. For example, in certain embodiments, the screens may remove that portion of the beads having diameters above 1.19 mm and below 0.84 mm.

The device which is utilized for powder-layering the beads is known to those skilled in the art. Such a device is described in detail in U.S. Pat. No. 5,132,142, hereby incorporated by reference.

The ratio of the powder feed rate to the solution feed rate is may be from about 1:10 to about 10:1, and more preferably from about 2:1 to about 1:1, at room temperature.

In preferred embodiments of the invention directed to immediate release powder-layered beads comprising a therapeutically effective agent, the formulation preferably provides an in-vitro dissolution rate for an immediate release (4-hour) dosage form, when measured by the USP Paddle Method at 100 rpm in 900 ml aqueous buffer, at 37° C. between 70 and 100% (by wt) drug released after 1 hour. USP Paddle Method is the Paddle Method described, e.g., in U.S. Pharmacopoeia XXII (1990). The dosage form preferably provides a peak plasma level of the opioid in-vivo from about 0.25 to about 4 hours after oral administration.

In embodiments of the present invention directed to extended release formulations, the powder-layered beads which are suitable for use as an immediate release product are coated with a extended release coating. The coating formulations of the present invention should be capable of producing a strong, continuous film that is smooth and elegant, capable of supporting pigments and other coating additives, non-toxic, inert, and tack-free.

The extended release formulations of the present invention provide a dissolution rate in-vitro of the dosage form, when measured by the USP Paddle Method at 100 rpm in 900 ml aqueous buffer, pH between about 1.6 and about 7.2 at 37° C., of from about 0 to about 40% (by wt) released after one hour, from about 5 to about 60 percent (by wt) released after 2 hours, from about 11 to about 70% (by wt) released after 4 hours, from about 15 to about 80% (by wt) released after 8 hours, from about 25 to abut 85% (by wt) released after 12 hours), and greater than 65% (by wt) released after 24 hours, the dosage form providing a duration of effect in-vivo for at least about 24 hours.

In preferred embodiment, the extended release dosage forms provide a dissolution rate in-vitro of the dosage form, when measured by the USP Paddle Method at 100 rpm in 900 ml aqueous buffer, pH between about 1.6 and about 7.2 at 37° C., of from about 0 to about 20% (by wt) released after one hour, from about 10 to about 40 percent (by wt) released after 2 hours, from about 20 to about 70% (by wt) released after 4 hours, from about 50 to about 80% (by wt) released after 8 hours, from about 60 to about 90% (by wt) released after 12 hours), and greater than 70% (by wt) released after 24 hours, the dosage form providing a duration of effect in-vitro for at least about 24 hours.

In order to obtain an extended release of the morphine sufficient to provide an analgesic effect for the desired duration of effect, the powder-layered beads may be coated with a sufficient amount of a controlled release agent such as a hydrophilic or a hydrophobic material to a weight gain level from about 2 to about 30 percent, although the overcoat may be greater depending upon the particular ingredients utilized in the coating, and the desired release rate, among other things. Extended release of other therapeutically effective agents sufficient to provide a desired duration of effect is carried out in a similar manner.

The solvent which is used for the controlled release material may be any pharmaceutically acceptable solvent, including water, methanol, ethanol, methylene chloride and mixtures thereof. It is preferable however, that the coatings be based upon aqueous dispersions of the hydrophobic material.

In certain preferred embodiments of the present invention, hydrophobic polymers such as the sustained-release coating comprise a pharmaceutically acceptable acrylic polymer, including but not limited to acrylic acid and methacrylic acid copolymers, methyl methacrylate copolymers, ethoxyethyl methacrylates, cyanoethyl methacrylate, aminoalkyl methacrylate copolymer, poly(acrylic acid), polymethacrylic acid, methacrylic acid alkylamide copolymer, poly(methyl methacrylate), poly(methacrylic acid anhydride), methyl methacrylate, polymethacrylate, polyacrylamide and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic coating is an acrylic resin lacquers used in the form of an aqueous dispersion, such as that which is commercially available form Rohm Pharma under the Tradename Eudragit®. In further preferred embodiments, the acrylic coating comprises a mixture of two acrylic resin lacquers commercially available from Rohm Pharma under the Tradenames Eudragit® RL 30 D and Eudragit® RS 30 D, respectively. Eudragit® RL 30 D and Eudragit® RS 30 D are copolymers of acrylic and methacrylic esters with a low content of quaternary ammonium groups, the molar ratio of ammonium groups to the remaining neutral (meth)acrylic esters being 1:20 in Eudragit® RL 30 and 1:40 in Eudragit® RS 30 D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a sustained-release formulation having a desirable dissolution profile. Desirable sustained-release formulations may be obtained, for instance, from a retardant coating derived from 100% Eudragit® RL, 50% Eudragit® RL and 50% Eudragit® RS, and 10% Eudragit® RL:Eudragit® 90% RS. Of course, one skilled in the art will recognize that other acrylic polymers may also be used, such as, for example, Eudragit® L.

In other preferred embodiments, the hydrophobic polymer which may be used for coating the substrates of the present invention is a hydrophobic cellulosic material such as ethylcellulose. Those skilled in the art will appreciate that other cellulosic polymers, including other alkyl cellulosic polymers, may be substituted for part of all of the ethylcellulose included in the hydrophobic polymer coatings of the present invention.

One commercially-available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

In embodiments of the present invention where the coating comprises an aqueous dispersion of a hydrophobic polymer, the inclusion of an effective amount of a plasticizer in the aqueous dispersion of hydrophobic polymer will further improve the physical properties of the film. For example, because ethyl-cellulose has a relatively high glass transition temperature and does not form flexible films under normal coating conditions, it is necessary to plasticize the ethylcellulose before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, acetyl tritethyl citrate, tributyl citrate, and triacetin, although it is possible that other water-insoluble plasticizers (such as acetylated monoglycerides, phthalate esters, castor oil, etc.) may be used. Triethyl citrate is especially preferred.

Examples of suitable plasticizers for the acrylic polymers of the present invention include citric acid esters such as triethyl citrate NF XVI, tributyl citrate, dibutyl phthalate, and possible 1,2-propylene glycol, polyethylene glycols, propylene glycol, diethyl phthalate, castor oil, and triacetin, although it is possible that other water-insoluble plasticizers (such as acetylated monoglycerides, phthalate esters, castor oil, etc.) may be used. Triethyl citrate is especially preferred.

The dissolution profile of the extended release formulations of the invention can be altered, for example, by varying the thickness of the hydrophobic coating, changing the particular hydrophobic material used, or altering the relative amounts of, e.g., different acrylic resin lacquers, altering the manner in which the plasticizer is added (e.g., when the sustained-release coating is derived from an aqueous dispersion of hydrophobic polymer), by varying the amount of plasticizer relative to hydrophobic polymer, by the inclusion of additional ingredients or excipients, by altering the method of manufacture, etc.

The plasticized aqueous dispersion of hydrophobic polymer may be applied onto the powder-layered beads by spraying using any suitable spray equipment known in the art. In a preferred method, a Wurster fluidized-bed system is used in which an air jet, injected from underneath, fluidizes the core material and effects drying while the coating is sprayed on. A sufficient amount of the aqueous dispersion of hydrophobic polymer to obtain the desired extended release of therapeutically effective agent is preferably applied, taking into account the manner of incorporation of the plasticizer, etc. After coating with the hydrophobic polymer, a further overcoat of a film-former, such as Opadry®, is optionally applied to the beads. This overcoat is provided, if at all, in order to substantially reduce agglomeration of the beads.

Next, the coated beads are cured in order to obtain a stabilized release rate of the therapeutically active agent.

When the coating comprises an aqueous dispersion of ethylcellulose, the coated substrate is preferably subjected to curing at a temperature greater than the glass transition temperature of the coating solution (i.e., ethylcellulose) and at a relative humidity from about 60% to about 100%, until the curing endpoint is reached, e.g., about 60° C. and a relative humidity from about 60% to about 100% for a time period from about 48 to about 72 hours.

In preferred embodiments of the present invention directed to the acrylic coating, a stabilized product is obtained by subjecting the coated substrate to oven curing at a temperature above the Tg of the plasticized acrylic polymer for the required time period, the optimum values for temperature and time for the particular formulation being determined experimentally. In certain embodiments of the present invention, the stabilized product is obtained via an oven curing conducted at a temperature of about 45° C. for a time period from about 24 to about 48 hours or longer.

The release of the therapeutically active agent from the sustained-release formulation of the present invention can be further influenced, i.e., adjusted to a desired rate, by the addition of one or more release-modifying agents, or by providing one or more passageways through the coating. The ratio of hydrophobic polymer to water soluble material is determined by, among other factors, the release rate required and the solubility characteristics of the materials selected.

The release-modifying agents which function as pore-formers may be organic or inorganic, and include materials that can be dissolved, extracted or leached from the coating in the environment of use. The pore-formers may comprise one or more hydrophilic polymers such as hydroxypropylmethylcellulose.

The sustained-release coatings of the present invention can also include erosion-promoting agents such as starch and gums.

The sustained-release coatings of the present invention can also include materials useful for making microporous lamina in the environment of use, such as polycarbonates comprised of linear polyesters of carbonic acid in which carbonate groups reoccur in the polymer chain.

The release-modifying agent may also comprise a semi-permeable polymer.

In other preferred embodiments of the present invention, the sustained release coating comprises hydrophilic polymers, such as cellulose ethers and protein derived materials. Of these polymers, the cellulose ethers, especially hydroxyalkylcelluloses and carboxyalkylcelluloses, are preferred. Other sustained release coating materials which may be used in the present invention include digestible, long chain ($C_8$–$C_{50}$, especially $C_{12}$–$C_{40}$), substituted or unsubstituted hydrocarbons, such as fatty acids, fatty alcohols, glyceryl esters of fatty acids, mineral and vegetable oils and waxes. Hydrocarbons having a melting point of between 25° and 90° C. are preferred. Of these long chain hydrocarbon materials, fatty (aliphatic) alcohols are preferred.

Polyalkylene glycols may also be used.

One suitable controlled release coating material comprises at least one water soluble hydroxyalkyl cellulose, at least one $C_{12}$–$C_{36}$, preferably $C_{14}$–$C_{22}$, aliphatic alcohol and, optionally, at least one polyalkylene glycol. The at least one hydroxyalkyl cellulose is preferably a hydroxy ($C_1$ to $C_6$) alkyl cellulose, such as hydroxypropylcellulose, hydroxypropylmethylcellulose and, especially, hydroxyethyl cellulose. The amount of the at least one hydroxyalkyl cellulose in the present oral dosage form will be determined, inter alia, by the precise rate of opioid release required. The at least one aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the at least one aliphatic alcohol in the present oral dosage form will be determined, as above, by the precise rate of opioid release required. It will also depend on whether at least one polyalkylene glycol is present in or absent from the oral dosage form. In the absence of at least one polyalkylene glycol, the oral dosage form preferably contains between 0.5% and 30% (by wt) of the at least one aliphatic alcohol. When at least one polyalkylene glycol is present in the oral dosage form, then the combined weight of the at least one aliphatic alcohol and the at least one polyalkylene glycol preferably constitutes between 0.5% and 30% (by wt) of the total dosage. Such coatings may be applied to the powder-layered beads by any known technique utilized by those of ordinary skill in the art.

In one embodiment, the ratio of, e.g., the at least one hydroxyalkyl cellulose or acrylic resin to the at least one aliphatic alcohol/polyalkylene glycol determines, to a considerable extend, the release rate of the opioid from the formulation. A ratio of the at least one hydroxyalkyl cellulose to the at least one aliphatic alcohol/polyalkylene glycol of between 1:2 and 1:4 is preferred, with a ratio of between 1:3 and 1:4 being particularly preferred.

The at least one polyalkylene glycol may be, for example, polypropylene glycol or, which is preferred, polyethylene glycol. The number average molecular weight of the at least one polyalkylene glycol is preferred between 1,000 and 15,000 especially between 1,500 and 12,000.

Another suitable controlled-release matrix would comprise an alkyl-cellulose (especially ethyl cellulose), a $C_{12}$ to $C_{36}$ aliphatic alcohol and, optionally, a polyalkylene glycol.

In certain preferred embodiments, the release-modifying agent is selected from hydroxypropylmethylcellulose, lactose, metal stearates, and mixtures of any of the foregoing.

The sustained-release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864 (all of which are hereby incorporated by reference). The passageway can have any shape such as round, triangular, square, elliptical, irregular, etc.

In certain embodiments of the present invention, an effective amount of opioid in immediate release form is included in the unit dose comprising the substrates of the present invention. The immediate release form of the opioid is included in an amount which is effective to shorten the time to maximum concentration of the opioid in the blood (e.g., plasma), such that the $T_{max}$ is shortened to a time of, e.g., from about 2 to about 4 hours. This causes the blood concentration curve to have an early peak rather than the substantially flattened curves currently recommended by those skilled in the art. It has been discovered that by including such an effective amount of immediate release opioid in the unit dose, the experience of relatively higher levels of pain in patients is significantly reduced. In such embodiments, an effective amount of the opioid in immediate release form may be coated onto the substrates of the present invention. For example, where the extended release opioid from the formulation is due to a controlled release coating, the immediate release layer would be overcoated on top of the controlled release coating. On the other hand, the immediate release layer may be coated onto the surface of substrates wherein the opioid is incorporated in a controlled release matrix. Where a plurality of the sustained release substrates comprising an effective unit dose of the opioid are incorporated into a hard gelatin capsule, the immediate release portion of the opioid dose may be incorporated into the gelatin capsule via inclusion of the sufficient amount of immediate release opioid as a powder or granulate within the capsule. Alternatively, the gelatin capsule itself may be coated with an immediate release layer of the opioid. One skilled in the art would recognize still other alternative manners of incorporating the immediate release opioid portion into the unit dose. Such alternatives are deemed to be encompassed by the appended claims.

The multiparticulate unit dose of morphine sulfate or other therapeutically effective agent may be contained within a hard gelatin capsule. Alternatively, the multiparticulate unit dose of morphine sulfate may be prepared as other dosage forms known to those skilled in the art, including sachets. The hard gelatin capsule may be opened and the powder-layered beads containing the drug may be sprinkled into fluids or mixed with food, in particular cool, soft food, such as applesauce or pudding, or a liquid such as water or orange juice.

In yet a further aspect of the invention, it has been found that all or part of the microcrystalline cellulose can be eliminated from powder layer formulations via the use of powder layer promoting agents comprising hydrous lactose impalpable. In certain preferred embodiments hydrous lactose impalpable comprises all or substantially all of the powder layer promoting agent. However, other pharmaceuically acceptable inert excipients can be substituted for a portion of the hydrous lactose impalpable including but not limited to microcrystalline cellulose. Thus there is provided an alternative method of making powder layered beads with reduced amounts or without microcrystalline cellulose. Preferred aspects of this method using hydrous lactose impalpable having a bulk density of from about 0.5 to about 0.7 g/ml and therapeutically effective agents having a bulk density of from about 0.4 to about 0.75 g/ml.

DETAILED DESCRIPTION OF THE PREFERRED EMBODIMENTS

The following examples illustrate various aspects of the present invention. They are not to be construed to limit the claims in any manner whatsoever.

EXAMPLE 1

Immediate Release Low-Load Bead Formulation

In Example 1, low-load morphine sulfate beads were prepared using a powder layering technique in a Glatt Rotor Processor. The beads were prepared by spraying the aqueous binder solution onto the beads 18/20 mesh to provide said beads with a tacky surface. Thereafter, a powder consisting of a homogeneous mixture of morphine sulfate and hydrous lactose impalpable powder was sprayed onto the beads once the beads have become tacky. The beads were then dried and sieved to obtain a powder-layered multiparticulate product having a suitable range of particle size. The formula of the morphine sulfate beads is set forth in Table 1 below:

TABLE 1

| Ingredient | Amt/Unit (mg) | Percent (%) |
| --- | --- | --- |
| Morphine Sulfate Powder | 30 mg | 14.3% |
| Lactose Hydrous Impalpable | 42.5 mg | 20.2% |
| PVP | 2.5 mg | 1.2% |
| Sugar Beads 18/20 | 125 mg | 59.4% |
| Purified Water | qs mg | — |
| Opadry Red YS-1-1841 | 10.5 mg | 4.9% |
| Total | 210.5 mg | 100.0% |

The lactose hydrous impalpable which is used is obtained from B.V. Hollandsche Melksuiker-fabriek (HMS), Uitgeest, Holland, and contains about 99.7% lactose monohydrate by weight. Typically, the lactose hydrous impalpable has a bulk density of 0.56 g/ml and a tapped bulk density of about 0.64 g/ml. The morphine sulfate has a bulk density of about 0.44 g/ml.

Upon completion of the powder-layering, the beads were then filled into gelatin capsules at a 30 mg morphine strength.

The capsules were then subjected to dissolution testing. Dissolution testing was conducted on the finished products via USP Apparatus II-(Paddle Method). The capsules were placed into 700 ml of simulated gastric fluid (without enzymes) for an hour at 100 rpm and 37° C., and it was determined that 90% of the morphine sulfate dissolved within one hour. The dissolution testing indicates that this product would be suitable as an immediate release formulation.

Figure 1:
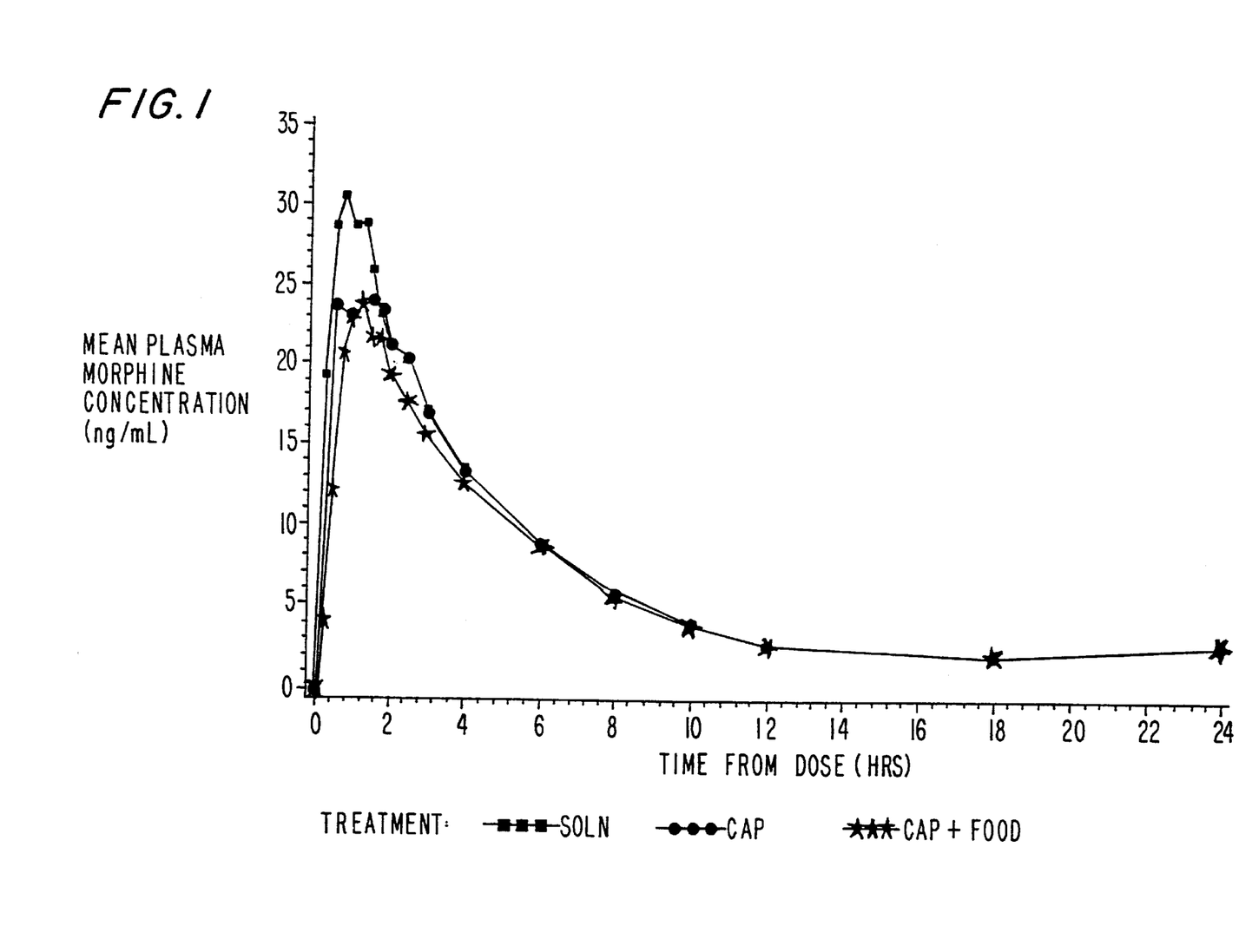
FIG. 1 is a graph depicting the blood level plasma of Example 1 both fasted and fed as compared to reference standard.

A human single dose bioavailability study was the conducted using the formulation of Example 1 and a reference standard (morphine sulfate solution, MSIR® solution commercially available from The Purdue Frederick Company), both dosed at 30 mg morphine sulfate per dose. The reference solution was dosed without food and the test bead product was dosed without food and with applesauce in a randomized crossover design. The in-vivo results are summarized in Table 2 below, and in FIG. 1.

TABLE 2

| Parameter | Morphine Sulfate Solution | MSIR Capsules | MSIR Capsules With Food |
| --- | --- | --- | --- |
| $C_{max}$ (ng/mL) | 37.09 (12.60) | 34.81 (11.94) | 28.63 (10.23) |
| $T_{max}$ (hours) | 0.85 (0.54) | 1.18 (0.70) | 1.36 (0.53) |
| AUC (0,24) (Hr-ng/mL) | 165.34 (35.40) | 155.69 (36.09) | 145.55 (37.53) |
| AUCINF (0, inf) (Hr-ng/mL) | 175.38 (36.74) | 166.07 (38.33) | 156.66 (40.25) |

This study included a minimal quantity of food (applesauce) and it appears that this product may have the potential of not being affected by food intake.

EXAMPLE 2

Immediate Release High-Load Bead Formulation

Beads with a high loading of morphine sulfate were produced with the use of a powder layering technique in the Glatt Rotor Processor. The hydrous lactose impalpable was blended with the morphine sulfate prior to manufacture. The manufacture was otherwise the same as in Example 1. The formulation of the high load beads is set forth in Table 3 below:

TABLE 3

| High Load Beads | | |
| --- | --- | --- |
| Ingredient | mg/unit | Percent (%) |
| Morphine Sulfate Pentahydrate Powder | 30.0 mg | 61.73% |
| Lactose Hydrous Impalpable | 6.0 mg | 12.35% |
| Povidone C-30 | 2.25 mg | 5.14% |
| Sugar Beads 30/35 | 7.75 mg | 15.95% |
| Opadry blue YS-1-10542A | 2.37 mg | 4.83% |
| Purified Water | qs | — |
| Total | 8.6 mg | 100.0% |

Upon completion of the powder-layering, the beads were then filled into gelatin capsules at a 30 mg morphine strength.

The capsules were then subjected to dissolution testing. Dissolution testing was conducted on the finished products via USP Apparatus II-(Paddle Method). The capsules were placed into 700 ml of simulated gastric fluid (without enzymes) for the first hour at 100 rpm and 37° C., and it was determined that 90% of the morphine sulfate dissolved within one hour. The dissolution testing indicates that this product would be suitable as an immediate release formulation.

EXAMPLE 3

Immediate Release High-Load Bead Formulation

A batch of morphine sulfate high-load beads was manufactured using an alternate method of powder layering. The formula is as follows:

TABLE 4

| Ingredient | mg/unit |
| --- | --- |
| Morphine Sulfate Powder | 50.0 mg |
| Lactose Hydrous Impalpable | 10.0 mg |
| Povidone | 1.5 mg |
| Sugar Beads 30/35 | 14.0 mg |
| Purified Water | qs |
| Opadry Blue YS-1-10542A | 3.9 mg |
| Total | 79.4 mg |

The high-load beads were prepared by first blending the morphine sulfate powder with the lactose hydrous impalpable. After blending, the Glatt rotor processor was charged with the sugar beads and 5 kg of morphine sulfate/lactose blend. The rotor processor was then activated, and the PVP 5% solution was sprayed into the batch. The 5 kg of morphine sulfate/lactose blend is layered without agglomeration occurring. Using this procedure, the PVP solution spray rate can be increased aggressively as compared to the method employed in other methods. The process commenced with first charging the rotor processor with the 30/35 beads and the morphine/lactose blend. After activating the rotor plate, set at 150 rpm, the PVP 5% w/w solution was sprayed onto the charge of beads and powder in a more aggressive manner. The inclusion of the MS/lactose blend along with the charge of 30/35 beads (12.6 kg) is done to eliminate twinning of the substrate beads. Because the starting beads are so small, the presence of minimal binding solution can cause agglomeration and batch failure. MS/lactose blend present with the substrate beads allows for preferential adhesion of the powder to the substrate beads versus bead to bead adhesion (a physical barrier to bead to bead surface). Once the 5 kg of powder blend is layered, powder feeders were activated and the process was completed when all powder blend was layered, while the PVP solution was being sprayed.

EXAMPLES 4–5

Extended Release Low-Load Bead Formulation

In Examples 4–5, an extended release coating was applied to morphine sulfate beads prepared identically to those of Examples 1 and 2. The formula for the functional coating of Examples 4 and 5 is set forth in Table 5 below:

TABLE 5

|  | Example 4 | | Example 5 | |
| --- | --- | --- | --- | --- |
| Ingredient | (mg) | % | (mg) | % |
| Morphine Base Beads | 189.5 mg | 86.7% | 189.5 mg | 83.0% |
| Retardant Coating | | | | |
| Eudragit RS 30D | 9.5 mg* | 4.3% | 15.2 mg* | 6.7% |
| Triethyl Citrate | 1.9 mg | 0.9% | 3.0 mg | 1.3% |
| Talc | 3.8 mg | 1.7% | 6.1 mg | 2.7% |
| Purified Water | qs Overcoat | — | — | — |
| Morphine Sulfate Powder | 3.0 mg | 1.4% | 3.0 mg | 1.3% |
| Opadry Red YS-1-1841 | 10.8 mg | 5.0% | 11.4 mg | 5.0% |
| Purified Water | qs | — | — | — |
| Total | 218.45 mg | 100.0% | 228.2 mg | 100.0% |

*Based on 27 mg MS5H$_2$O Equivalent of Immediate Release Beads of Example 1

The extended release coating is manufactured as follows:

The Eudragit RS 30D is plasticized with triethyl citrate and the talc for approximately 30 minutes. A load of the morphine sulfate beads is charged into a Wurster Insert of a Glatt equipped with a 1.2 mm spray nozzle and the beads are coated to a weight gain of 5% and 8%, respectively. The final protective Opadry dispersion overcoat is then applied in the Wurster Insert. Upon completion the beads are cured for two days in a dry oven of 45$20$ C. The cured beads were then filled into gelatin capsules at a 30 mg strength.

Dissolution testing were conducted on the gelatin capsules via U.S.P. Apparatus II (Paddle Method). The capsules were placed into 700 ml of simulated gastric fluid (without enzymes) for the first hour at 100 rpm and 37° C., and then in the same vessel 200 ml of phosphate buffer was added to make 900 ml of simulated gastric fluid (without enzymes) after the first hour. The results of the percent of morphine sulfate dissolved in relation to time, are set forth in Table 6 below:

TABLE 6

| Percent Morphine Sulfate Dissolved | | |
| --- | --- | --- |
| Time | Example 4 | Example 5 |
| 1 hour | 11.9% | 10.2% |
| 2 hours | 15.4% | 11.3% |
| 4 hours | 28.1% | 12.8% |
| 8 hours | 58.3% | 16.4% |
| 12 hours | 79.2% | 29.6% |
| 18 hours | 92.0% | 58.1% |
| 24 hours | 96.6% | 73.2% |

Figure 2:
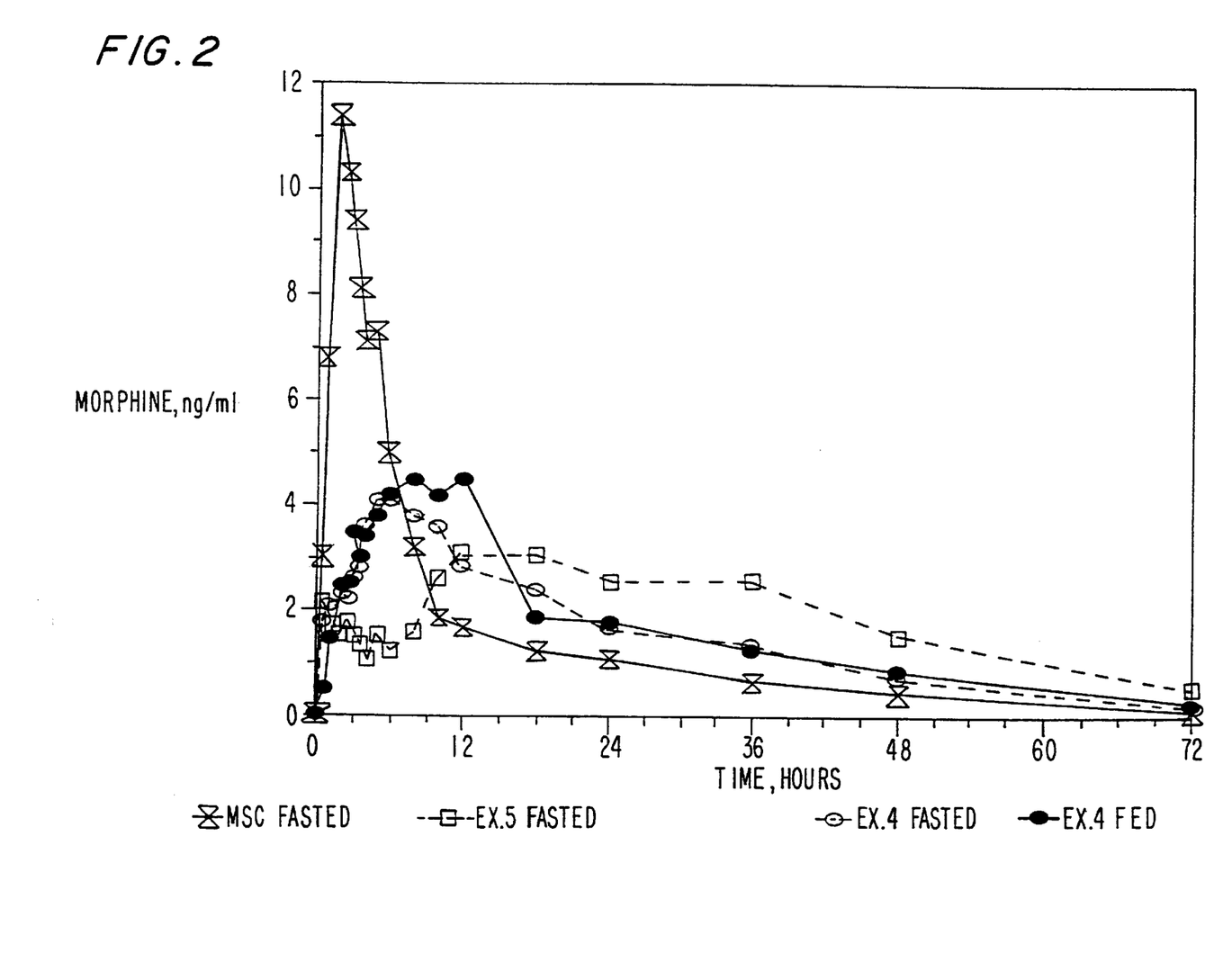
FIG. 2 is a graph depicting the blood plasma levels obtained with the formulation of Examples 4 and 5.

A bioavailability study was conducted with Examples 4 and 5 dosed once-a-day, using the commercially available product MS Contin® which is designed for twice daily dosing. Examples 4 and 5 are designed for once daily dosing. The results are provided in Table 7 below, and are graphically depicted in FIG. 2:

TABLE 7

| Example | AUC | $T_{max}$ | $C_{max}$ |
| --- | --- | --- | --- |
| MS Contin ® | 99 | 2.2 | 13.0 |
| Example 4 - Fasted | 107 | 5.9 | 5.4 |
| Example 4 - Fed | 116 | 6.9 | 5.9 |
| Example 5 - Fasted | 136 | 15.0 | 3.9 |

From the above data it can be seen that the formulation of Example 4 is an ideal for a once-a-day product without a food effect. Example 5 would be for dosing for at least once-a-day or substantially longer.

EXAMPLE 6

Beads with a high-load of morphine sulfate were produced with the use of a powder layering technique in the Glatt Rotor Processor. Lactose was blended with the morphine sulfate prior to manufacture. The manufacture was otherwise the same as in Example 2 above. The formulation of the high load beads is set forth in Table 8 below:

TABLE 8

| High-Load Beads | | |
| --- | --- | --- |
| Ingredient | mg/unit | Percent (%) |
| Morphine Sulfate Powder | 30.3 mg | 63.3% |
| Lactose Hydrous Impalpable | 6.0 mg | 12.7% |
| Povidone C-30 | 1.25 mg | 2.6% |
| Sugar Beads | 7.75 mg | 16.4% |
| Opadry | 2.37 mg | 5.0% |
| Purified Water | qs | — |
| Total | 47.37 mg | 100.0% |

The sustained release coating comprises a mixture of acrylic polymers (i.e., Eudragit® RS and RL). A hydroxypropylmethylcellulose (HPMC) protective coat is also included between the Eudragit layer and the morphine immediate release layer to further enhance stability. The formula of the sustained release coating of Example 6 is set forth in Table 9 below:

TABLE 9

| Ingredient | Amt/Unit (mg) | Percent (%) |
| --- | --- | --- |
| Morphine (high load) base beads | 42.63 mg | 78.8% |
| Retardant Coating | | |
| Eudragit RS 30D | 2.1 mg | 3.9% |
| Eudragit RL 30D | 0.05 mg | 0.1% |
| Triethyl Citrate | 0.45 mg | 0.8% |
| Talc | 0.85 mg | 1.6% |
| Overcoatings | | |
| Opadry Blue YS-1-10542A | 2.45 mg | 4.5% |
| Purified Water | qs | — |
| Morphine Sulfate Powder | 3.0 mg | 5.5% |
| Opadry Blue YS-1-10542A | 2.55 mg | 4.8% |
| Purified Water | qs | — |
| Total | 54.08 mg | 100.0% |

The extended release coating and the immediate release overcoat were applied as follows: The Eudragit RL 30D is plasticized with triethyl citrate and talc for approximately 30 minutes. A load of the morphine sulfate beads is charged into a Wurster Insert of a Glatt equipped with a 1.2 mm spray nozzle and the beads are coated to a weight gain of 5%. The final protective Opadry dispersion overcoat is then applied in the Wurster Insert. Upon completion the beads are cured for two days in a dry oven at 45° C. The cured beads were then filled into gelatin capsules at a 30 mg strength. The cured beads were then filled into gelatin capsules at a strength of 30 mg.

The capsules were then subjected to dissolution testing. Dissolution testing was conducted on the finished products via USP Apparatus II-(Paddle Method). The capsules were placed into 700 ml of simulated gastric fluid (without enzymes) for the first hour at 100 rpm and 37° C., and then in the same vessel 200 ml of phosphate buffer is added to make 900 ml of simulated gastric fluid (without enzymes). The results of dissolution testing are set forth in Table 10 below:

TABLE 10

| Time | Percent Morphine Sulfate Dissolved |
|---|---|
| 1 hour | 11.7% |
| 2 hours | 12.1% |
| 4 hours | 22.0% |
| 8 hours | 45.3% |
| 12 hours | 63.7% |
| 18 hours | 81.8% |
| 24 hours | 92.5% |

The dissolution testing as set forth in Table 10 indicates that this product would be suitable for once-a-day administration.

A human single dose bioavailability study was then conducted using a reference standard (MS Contin®), which is approved for twice-a-day administration and the formulation of Example 6, which were designed for once-a-day administration. The in-vivo results are summarized in Table 11 below.

TABLE 11

| Group | AUC | $C_{max}$ (ng/ml) | $T_{max}$ (Hours) |
|---|---|---|---|
| MS Contin Tablets | 114 | 11.6 | 2.8 |
| Example 6 | 41 | 4.0 | 12.9 |

The above data show that Example 6 is suitable for once-a-day administration.

COMPARATIVE EXAMPLE 7

Morphine Sulfate High-Load Multidose Beads

A batch of morphine sulfate high-load beads was manufactured using the process of powder layering on the rotor processor of the Versa Glatt. The formula made is as follows:

TABLE 12

| Ingredient | Amt/Unit (mg) |
|---|---|
| Morphine Sulfate H₂O Powder | 30 mg |
| Povidone | 1.25 mg |
| Sugar Beads 25/30 | — |
| Purified Water | 7.75 mg |
| Opadry Blue (YS-1-10542A) | 2.05 mg |
| Total | 41.01 mg |

Povidone was dissolved in water to yield a 5% w/w solution. Next, Opadry Blue was dissolved in water to yield a 15% w/w dispersion for final filmcoating. The rotor processor was charged with the 25/30 sugar beads, and the powder was then added onto the beads via a powder feeder and the binder solution was simultaneously sprayed on the beads while they are rotating in the Glatt rotor processor. The beads produced were relatively soft.

A final protective overcoat of the Opadry blue was then applied in the rotor processor.

The beads were then overcoated with a controlled release functional coating with the following:

TABLE 13

| Ingredient | Amt/Unit | Amt/Batch |
|---|---|---|
| Morphine Sulfate High-load Beads | 40.05 mg | 600.0 g |
| Opadry Blue YS-1-10542A | 1.35 mg | 20.2 mg |
| Purified Water | — | qs |
| Eudragit RS30D | 1.65 mg | 24.7 g |
| Triethyl Citrate | 0.35 mg | 5.2 g |
| Purified Water | — | qs |
| Opadry Blue YS-1-10542A | 2.3 mg | 34.5 g |
| Purified Water | — | qs |
| Total | 46.35 mg | 694.3 g |

The batch was processed in the Wurster insert of the versa glatt and cured at 45° C. dry for two days and dissolution for this batch is as follows:

TABLE 14

| Time (hr) | % Dissolved |
|---|---|
| 1 | 4.6 |
| 2 | 6.9 |
| 4 | 25.6 |
| 8 | 58.7 |
| 12 | 78.7 |
| 18 | 94.7 |
| 24 | 102.4 |

The beads produced had unsatisfactory friability, were fragile and an inordinate amount of fine particles when a coating was applied to the beads.

EXAMPLE 8

A batch of morphine sulfate high-load beads was manufactured using an alternate method of powder layering. The formula is as follows:

TABLE 15

| Ingredient | Amt/Unit |
|---|---|
| Morphine Sulfate Powder | 54.0 mg |
| Lactose Hydrous Impalpable | 10.8 mg |
| Povidone | 2.25 mg |
| Sugar Beads 30/35 | 50.1 mg |
| Purified Water | — |
| Opadry Blue YS-1-10542A | 6.1 mg |
| Total | 123.25 mg |

The high-load beads were prepared by first blending the morphine sulfate powder with the lactose hydrous imp. After blending, the Glatt rotor processor was charged with the sugar beads and 5 kg of morphine sulfate/lactose blend. The rotor processor was then activated, and the PVP 5% solution was sprayed into the batch. The 5 kg of morphine sulfate/lactose blend is layered without agglomeration occurring. Using this procedure, the PVP solution spray rate can be increased aggressively as compared to the method employed in other methods. Once the 5 kg of powder blend is layered, powder feeders were activated and the process was completed when all powder blend was layered, while the PVP solution was being sprayed.

EXAMPLE 9

In Example 9, the low-load morphine sulfate beads were manufactured in the same manner as outlined in Example 1. The formula was as follows:

TABLE 16

| Ingredient | Amt/Unit (mg) | Percent (%) |
|---|---|---|
| Morphine Sulfate Powder | 30.0 mg | 14.3 |
| Lactose Hydrous Impalpable | 42.5 mg | 20.2 |
| PVP | 2.5 mg | 1.2 |
| Sugar Beads 18/20 | 125.0 mg | 59.4 |
| Purified Water | qs | — |
| Opadry Red YS-1-1841 | 10.5 mg | 4.9 |
| Total | 210.5 mg | 100.0% |

A sustained release coating of ethylcellulose with 5% HPMC as pore former was then applied. A commercial product which is an ethylcellulose dispersion known as Aquacoat® was used.

The sustained release coating was manufactured as follows:

The pore former Methocel E5 Premium (HPMC), was dispersed and dissolved in enough purified water to yield a 2% w/w solution.

An Aquacoat dispersion was plasticized with triethyl citrate for approximately 30 minutes. After 30 minutes the HPMC dispersion was mixed into the plasticized Aquacoat dispersion, and blended for an additional 15–30 minutes. A load of the morphine sulfate beads was charged into a Uniglatt Wurster Insert equipped with a 1.2 mm fluid nozzle. The beads were then film coated with the Aquacoat/HPMC dispersion (in a ratio of 95:5) to a weight gain of 5%.

The controlled release coating formula used in Example 9 is set forth in Table 17 below:

TABLE 17

| Ingredient | Amt/Unit |
|---|---|
| Morphine Sulfate Base Beads | 210.5 mg |
| Aquacoat ECD 30 (solids) | 10.0 mg |
| Methocel E5 Premium | 0.5 mg |
| Triethyl Citrate | 2.1 mg |
| Purified Water | qs |
| Opadry Red YS-1-1841 | 11.7 mg |
| Purified Water | qs |
| Total | 234.8 mg |

After completion of the application of the sustained release coating process, the coated beads were discharged from the Wurster Insert into a curing tray and cured in a temperature/humidity chamber at 60° C./80% RH for 72 hours. Upon completion of this curing step, the beads were dried to a LOD of 4% or less and were given a final overcoat of Opadry Red YS-1-1841 (15% w/w solution) using the Uniglatt Wurster Insert. The beads were then filled into hard gelatin capsules using a capsule filling machine to obtain the finished product.

The finished product was then subjected to dissolution testing via USP Apparatus II (paddle method), 100 rpm, 37° C., 700 ml simulated gastric fluid (without enzyme) for one hour, and then 900 ml simulated gastric fluid (without enzymes after first hour).

The results are as follows:

TABLE 18

| Time (hours) | % Morphine Dissolved |
|---|---|
| 1 | 16.9 |
| 2 | 29.6 |
| 4 | 52.3 |
| 8 | 79.8 |
| 12 | 92.8 |
| 18 | 101.4 |
| 24 | 104.7 |

EXAMPLE 10

In Example 10, morphine sulfate controlled release beads with a controlled release coating of 5% w/w (including 3% HPMC as a pore former, by weight of the coating), were prepared.

Morphine sulfate controlled release beads was manufactured with a 5% w/w controlled release coating and a 5% HPMC overcoat. The morphine sulfate base beads to which the controlled release coating was applied are prepared as described in Example 9. Thereafter, the controlled release coating was prepared and applied to the beads to a weight gain of 5%. Further information concerning the formulation of Example 10 is provided in Table 19 below:

TABLE 19

| Ingredient | Amt/Unit |
|---|---|
| Morphine Sulfate Base Beads | 210.5 mg |
| Aquacoat ECD 30 (solids) | 10.2 mg |
| Methocel E5 Premium | 0.3 mg |
| Triethyl Citrate | 2.1 mg |
| Purified Water | qs |
| Opadry Red YS-1-1841 | 11.7 mg |
| Purified Water | qs |
| Total | 234.8 mg |

The manufacturing process and curing and encapsulation technique used was the same as Example 10 as per Example 9, the difference being that the beads were filmcoated with an Aquacoat/HPMC (97:3) dispersion in Example 10.

The results of dissolution testing conducted in the same manner as per Example 21 are set forth in Table 20 below:

TABLE 20

| Time (hours) | % Morphine Dissolved |
|---|---|
| 1 | 17.8 |
| 2 | 28.4 |
| 4 | 46.7 |
| 8 | 73.1 |
| 12 | 86.0 |
| 24 | 99.0 |

A human bioavailability study was then conducted with the capsules produced in Examples 9 and 10 using MS Contin as the reference. Examples 9 and 10 were designed for once daily dosing. In this study the effect of food was also investigated. Table 21 provides a summary of the results obtained.

TABLE 21

| Study Group | AUC | $T_{max}$ | $C_{max}$ |
| --- | --- | --- | --- |
| Ex. 9 (95:5 Fasted) | 93 | 3.6 | 7.0 |
| Ex. 10 (97:3 Fasted) | 101 | 5.6 | 5.9 |
| Ex. 10 (97:3 Fed) | 96 | 7.8 | 5.9 |
| MS Contin (Fasted) | 103 | 2.3 | 13.0 |

Figure 3:
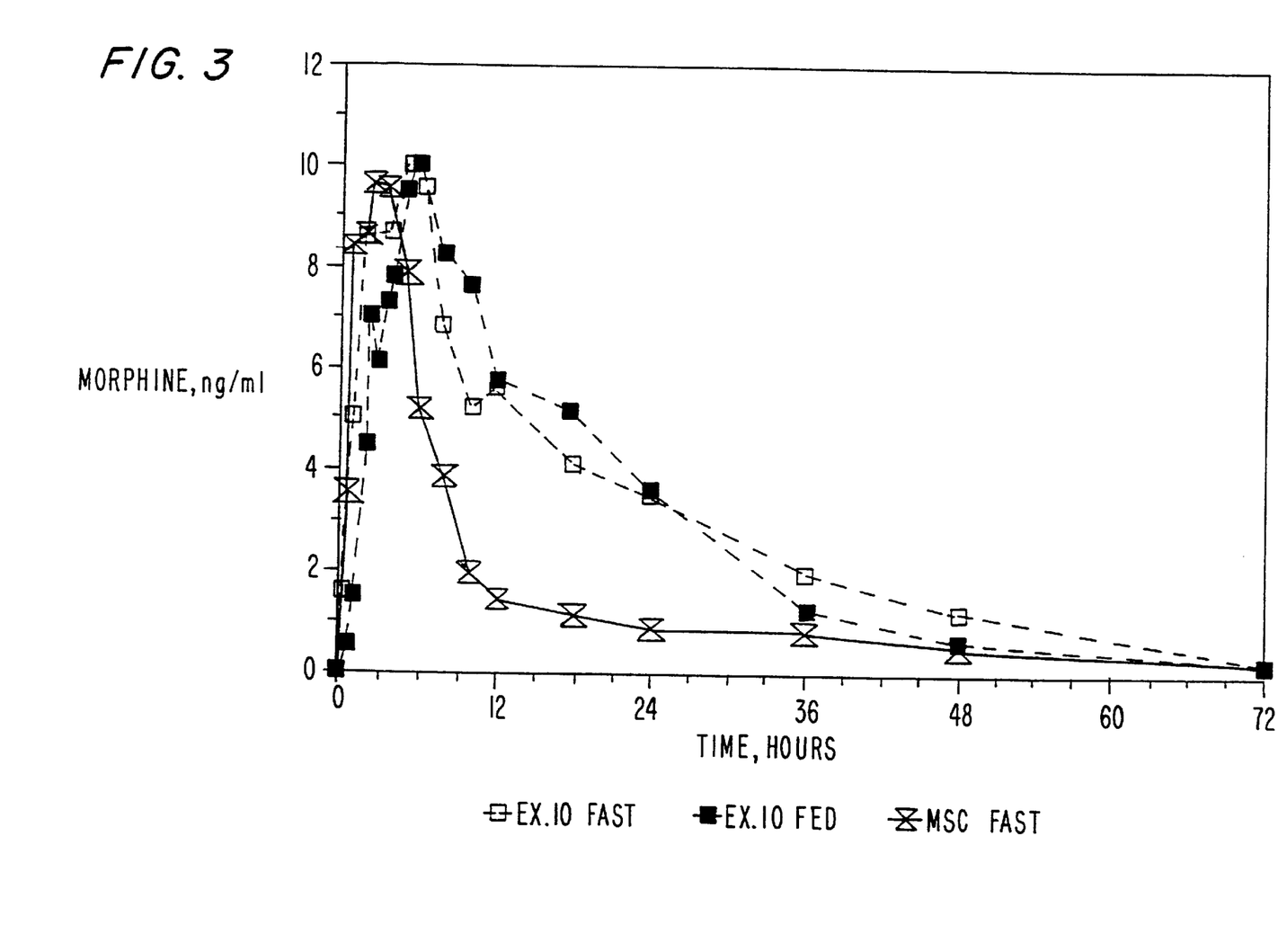
FIG. 3 is a graph depicting the blood plasma levels obtained with the formulation Example 10, both fasted and fed, as compared to a reference standard.

The bioavailability of Example 10 is graphically depicted in FIG. 3, showing that there is no food effect.

EXAMPLE 11

Immediate Release Low-Load Codeine Bead Formulation

In this example, a low-load bead formulation is prepared using a powder layering technique in a Glatt Rotor Processor. Following the procedure of Example 1, the beads are prepared by spraying the aqueous binder solution onto the beads 18/20 mesh to provide the beads with a tacky surface. Thereafter, a powder consisting of a homogeneous mixture of codeine phosphate USP powder—and hydrous lactose impalpable powder is sprayed onto the beads after the beads have become tacky. The beads are then dried and sieved to obtain a powder-layered multiparticulate product having a suitable range of particle size. The formula of the codeine phosphate USP powder beads is set forth in Table 22 below:

TABLE 22

| Ingredient | Amt/Unit (mg) | Percent (%) |
| --- | --- | --- |
| Codeine Phosphate USP Special Powder | 30.0 mg | 14.3% |
| Lactose Hydrous Impalpable | 42.5 mg | 20.2% |
| PVP | 2.5 mg | 1.2% |
| Sugar Beads 18/20 | 125.0 mg | 59.4% |
| Purified Water | qs | — |
| Opadry Red YS-1-1841 | 10.5 mg | 4.9% |
| Total | 210.5 mg | 100.0% |

The lactose hydrous impalpable which is used has a bulk density of 0.56 g/ml and a tapped bulk density of about 0.64 g/ml. The codeine phosphate USP special powder has a bulk density of about 0.55 g/ml. After completion of the powder-layering, the beads are filled into gelatin capsules at a 30 mg codeine strength.

EXAMPLE 12–15

Immediate Release Low-Load Bead Formulations

In these examples, further low-load bead formulations are prepared using the same powder layering technique described in Example 11 using a Glatt Rotor Processor are undertaken. The lactose hydrous impalpable used has a bulk density of 0.56 g/ml and a tapped bulk density of about 0.64 g/ml.
Example 12: acetaminophen—bulk density of about 0.42 g/ml.
Example 13: metoclopramide HCl—bulk density of about 0.5 g/ml.
Example 14: codeine sulfate USP medium crystals-fine—bulk density of about 0.6 g/ml.
Example 15: tramadol HCl—bulk density of about 0.42 g/ml.

In each example, after completion of the powder-layering, the beads are filled into gelatin capsules.

EXAMPLES 16–17

Extended Release Low-Load Bead Formulation

In these examples, the techniques of Examples 4–5 are repeated to provide an extended release coating to the codeine phosphate USP special powder beads prepared in Example 11. The formula for the coatings of Examples 16 and 17 are set forth in Table 23 below:

TABLE 23

| | Example 16 | | Example 17 | |
| --- | --- | --- | --- | --- |
| Ingredient | (mg) | % | (mg) | % |
| Codeine Phosphate USP Special Powder Beads | 189.5 mg | 86.7% | 189.5 mg | 83.0% |
| Retardant Coating | | | | |
| Eudragit RS 30D | 9.5 mg* | 4.3% | 15.2 mg* | 6.7% |
| Triethyl Citrate | 1.9 mg | 0.9% | 3.0 mg | 1.3% |
| Talc | 3.8 mg | 1.7% | 6.1 mg | 2.7% |
| Purified Water | qs | — | — | — |
| Overcoat | | | | |
| Codeine Phosphate USP Special Powder Beads | 3.0 mg | 1.4% | 3.0 mg | 1.3% |
| Opadry Red YS-1-1841 | 10.8 mg | 5.0% | 11.4 mg | 5.0% |
| Purified Water | qs | — | — — | |
| Total | 218.45 mg | 100.0% | 228.2 mg | 100.0% |

The extended release coating is manufactured as follows:

The Eudragit RS 30D is plasticized with triethyl citrate and talc for approximately 30 minutes. A load of the codeine phosphate USP special powder beads is charged into a Wurster Insert of a Glatt equipped with a 1.2 mm spray nozzle and the beads are coated to a weight gain of 5% and 8%, respectively. The final protective Opadry dispersion overcoat is then applied in the Wurster Insert. Upon completion the beads are cured for two days in a dry oven of 45° C. The cured beads were then filled into gelatin capsules at a 30 mg strength.

The examples provided above are not meant to be exclusive. Many other variations of the present invention would be obvious to those skilled in the art, and are contemplated to be within the scope of the appended claims. For example, it is contemplated that other pharmaceutically acceptable salts or complexes of morphine may be used instead of part or all of the preferred morphine salt, morphine sulfate. Likewise, it is contemplated that other pharmaceutically acceptable materials may be used to impart a sustained release to the morphine formulations of the invention, e.g., in a sustained release coating.

What is claimed is:

1. A bioavailable immediate release multi-particulate oral dosage form of a therapeutically effective agent, comprising:
a plurality of pharmaceutically acceptable inert beads having a diameter from about 0.1 mm to about 2.5 mm, said beads powder-layered with a homogeneous mixture of a therapeutically effective agent having a bulk density of from about 0.2 to about 0.8 g/ml and a pharmaceutically acceptable powdered material consisting essentially of hydrous lactose impalpable having a bulk density from about 0.4 to about 0.9 g/ml.

2. The dosage form of claim 1, wherein said therapeutically effective agent has a bulk density of from about 0.4 to about 0.75 g/ml.

3. The dosage form of claim 1, wherein said hydrous lactose impalpable has a bulk density of from about 0.5 to about 0.7 g/ml.

4. The dosage form of claim 1, wherein said therapeutically effective agent is selected from the group consisting of acetaminophen, metoclopramide, codeine phosphate USP Special powder, codeine phosphate USP powder, codeine sulfate USP Medium crystals-fine, doxycycline metaphosphate sodium complex, tramadol, theophylline anhydrous, aminophylline USP, diclofenac sodium and sodium ascorbate.

5. The dosage form of claim 1 which provides a peak plasma level of said therapeutically effective agent from about 0.25 to about 2 hours after administration.

6. The dosage form of claim 1, wherein said beads are powder-layered to a weight gain of at least about 50%.

7. The dosage form of claim 1, wherein said powder-layered beads further comprise an extended release overcoat comprising an effective amount of a hydrophobic material providing a dissolution rate in-vitro of the dosage form, when measured by the USP Paddle Method at 100 rpm in 900 ml aqueous buffer, pH between about 1.6 and about 7.2 at 37° C., from about 0 to about 40.0% (by wt) released after 1 hour, from about 5 to about 60% (by wt) released after 2 hours, from about 11 to about 70% (by wt) released after 4 hours, from about 15 to about 80% (by wt) released after 8 hours, from about 25 to about 85% (by wt) released after 12 hours, and greater than about 65% (by wt) released after 24 hours, said dosage form providing a duration of effective of at least about 24 hours.

8. The dosage form of claim 1, wherein said plurality of beads are contained within a hard gelatin capsule.

9. The dosage form of claim 7, wherein said powder-layered beads are coated with a hydrophobic material selected from the group consisting of an acrylic polymer; an alkylcellulose; shellac; zein; hydrogenated vegetable oil; hydrogenated castor oil; a wax either alone or together with a fatty alcohol; and mixtures of any of the foregoing.

10. The dosage form of claim 1, wherein powder-layered beads are coated with a hydrophilic material.

11. The dosage form of claim 10, wherein said hydrophilic material is hydroxypropylmethylcellulose.

12. A method for preparing an oral dosage form of powder-layered beads containing a therapeutically effective agent, comprising:
   a) admixing a therapeutically effective agent with a pharmaceutically acceptable powdered material consisting essentially of hydrous lactose impalpable having a bulk density of from about 75% to about 125% of the bulk density of said therapeutically effective agent to form a homogeneous powder mixture;
   b) spraying an aqueous binder solution onto inert beads having a diameter from about 0.1 mm to about 2.5 mm, to provide said beads with a tacky surface; and
   c) powder-layering said tacky beads with said homogeneous powder mixture until said beads achieve a weight gain of at least about 10% to about 100%.

13. The method of claim 12 further comprising the steps of:
   e) drying said powder-layered beads; and
   f) sieving the powder-layered beads to obtain a powder-layered multiparticulate product having a suitable range of particle size.

14. The method of claim 12, wherein said hydrous lactose impalpable has a bulk density of from about 0.4 to about 0.9 g/ml.

15. The method of claim 14, wherein said hydrous lactose impalpable has a bulk density of from about 0.5 to about 0.7 g/ml.

16. The method of claim 12, wherein said therapeutically effective agent has a bulk density of from about homogeneous mixture of a therapeutically effective agent having a bulk density of from about 0.2 to about 0.8 g/ml.

17. The method of claim 16, wherein said therapeutically effective agent has a bulk density of from about 0.4 to about 0.75 g/ml.

18. The method of claim 12, wherein said binder solution is selected from the group consisting of polyvinylpyrrolidone, celluloses, gelatins, gums, acrylic polymers, starches and mixtures of any of the foregoing.

19. The method of claim 12, further comprising incorporating a plurality of said powder-layered beads into a unit dose.

20. The method of claim 12, further comprising coating said powder-layered spheres with a sustained-release overcoat comprising an effective amount of a hydrophobic material selected from the group consisting of an acrylic polymer, an alkylcellulose, shellac, zein, hydrogenated vegetable oil, hydrogenated castor oil, and mixtures of any of the foregoing to provide a sustained release of said drug in the gastrointestinal tract for at least about 12–24 hours.

21. The method of claim 20, further comprising incorporating an effective amount of said coated, powder-layered spheres into a unit dose.

22. The method of claim 19, further comprising placing said unit dose into a hard gelatin capsule.

23. The method of claim 12, further comprising coating said powder-layered spheres with an sustained-release overcoat comprising an effective amount of hydrophilic material.

24. The method of claim 12, wherein said therapeutically effective agent is selected from the group consisting of acetaminophen, metoclopramide, codeine phosphate USP special powder, codeine phosphate USP powder, codeine sulfate USP medium crystals-fine, doxycycline metaphosphate sodium complex, tramadol, theophylline anhydrous, aminophylline USP, diclofenac sodium and sodium ascorbate.

25. A method of treating a mammal with an oral formulation containing a therapeutically effective agent, comprising:
   spraying an aqueous binder solution onto inert pharmaceutical beads having a diameter from about 0.1 mm to about 2.5 mm, to provide said beads with a tacky surface;
   powder-layering said tacky beads with a powder consisting essentially of a homogeneous mixture of a therapeutically effective agent having a density range from about 0.2 to about 0.8 g/ml and hydrous lactose impalpable having a density range from about 0.4 to about 0.9 g/ml until said beads achieve a weight gain drug of at least 10% to about a 100-fold increase in weight;
   drying said powder-layered beads;
   sieving the powder-layered beads to obtain a powder-layered multiparticulate product having a suitable range of particle size;
   incorporating a plurality of said therapeutically effective agent beads into a unit dose containing an effective amount of said therapeutically effective agent; and
   orally administering said unit dose to a mammal in need thereof.

26. The method of claim 25, wherein said hydrous lactose impalpable has a bulk density of from about 0.5 to about 0.7 g/ml.

27. The method of claim 25, wherein said therapeutically effective agent has a bulk density of from about 0.4 to about 0.75 g/ml.

28. The method of claim 25, wherein said unit dose provides effective blood plasma levels of said therapeutically effective agent for about 4 hours.

29. The method of claim 25, wherein said unit dose provides effective blood plasma levels of said therapeutically effective agent for about 24 hours.

30. The method of claim 25, further comprising coating said powder-layered beads with a sustained-release overcoat comprising an effective amount of a hydrophobic material selected from the group consisting of an acrylic polymer; an alkylcellulose; shellac; zein; hydrogenated vegetable oil; hydrogenated castor oil; a wax, either alone or together with a fatty alcohol; and mixtures of any of the foregoing to provide a sustained release of said therapeutically effective agent in the gastrointestinal tract for at least about 24 hours.

31. The method of claim 25, wherein said therapeutically effective agent is selected from the group consisting of acetaminophen, metoclopramide, codeine phosphate USP special powder, codeine phosphate USP powder, codeine sulfate USP medium crystals-fine, doxycycline metaphosphate sodium complex, tramadol, theophylline anhydrous, aminophylline USP, diclofenac sodium and sodium ascorbate.

32. The method of claim 25, further comprising coating said powder-layered beads with a sustained-release overcoat comprising an amount of a hydrophilic material effective to provide sustained release of said therapeutically effective agent.

33. A method of powder layering a substrate with a therapeutically effective agent having a bulk density of from about 0.2 to about 0.8 g/ml, comprising powder layering said substrate with said therapeutically effective agent utilizing hydrous lactose impalpable having a bulk density of from about 0.4 to about 0.9 g/ml.

34. The method of claim 33, wherein said hydrous lactose impalpable has a bulk density of from about 0.5 to about 0.7 g/ml.

* * * * *